(12) United States Patent
Anjing et al.

(10) Patent No.: US 8,299,127 B2
(45) Date of Patent: Oct. 30, 2012

(54) METHOD AND COMPOSITION FOR EVENLY APPLYING WATER SOLUBLE ACTIVES

(75) Inventors: Lou Anjing, Seymour, CT (US); Qiu Qiang, Trumbull, CT (US)

(73) Assignee: Conopco, Inc., Englewood Cliffs, NJ (US)

(*) Notice: Subject to any disclaimer, the term of this patent is extended or adjusted under 35 U.S.C. 154(b) by 471 days.

(21) Appl. No.: 12/402,238

(22) Filed: Mar. 11, 2009

(65) Prior Publication Data
US 2010/0234474 A1 Sep. 16, 2010

(51) Int. Cl.
*A61K 31/121* (2006.01)
(52) U.S. Cl. ........................ 514/675; 514/183
(58) Field of Classification Search .............. 514/183, 514/675
See application file for complete search history.

(56) References Cited

U.S. PATENT DOCUMENTS

| | | | |
|---|---|---|---|
| 4,104,403 A | 8/1978 | Barker et al. | 424/365 |
| 4,385,049 A | 5/1983 | Cuca | 424/167 |
| 4,405,616 A | 9/1983 | Rajadhyaksha | 424/244 |
| 4,606,913 A | 8/1986 | Aronson et al. | 424/59 |
| 4,886,783 A | 12/1989 | Minaskanian et al. | 574/29 |
| 4,981,845 A | 1/1991 | Pereira | 514/557 |
| 5,118,845 A | 6/1992 | Peck et al. | 564/215 |
| 5,232,688 A | 8/1993 | Ziegler et al. | 424/59 |
| 5,387,417 A | 2/1995 | Rentsch | 424/401 |
| 5,412,004 A * | 5/1995 | Tachibana et al. | 524/27 |
| 5,612,044 A | 3/1997 | Suares et al. | 424/401 |
| 5,645,822 A | 7/1997 | Meyer et al. | 424/59 |
| 5,720,948 A | 2/1998 | Brucks et al. | 424/78.02 |
| 5,750,092 A | 5/1998 | Meyer et al. | 424/59 |
| 5,756,075 A | 5/1998 | Meyer | 424/59 |
| 5,833,973 A | 11/1998 | Dobkowski et al. | |
| 5,908,707 A | 6/1999 | Cabell et al. | |
| 5,977,194 A | 11/1999 | Mork et al. | 521/61 |
| 6,069,169 A * | 5/2000 | Ptchelintsev et al. | 514/532 |
| 6,147,131 A | 11/2000 | Mork et al. | 521/61 |
| 6,231,837 B1 | 5/2001 | Stroud et al. | 424/59 |
| 6,303,834 B1 | 10/2001 | Mork et al. | 568/614 |
| 6,352,701 B1 * | 3/2002 | Scholz et al. | 424/405 |
| 6,383,503 B1 | 5/2002 | Bleckmann et al. | 424/401 |
| 6,423,626 B1 * | 7/2002 | Srinivasan et al. | 438/618 |
| 6,475,500 B2 | 11/2002 | Vatter et al. | 424/401 |
| 6,524,598 B2 | 2/2003 | Sunkel et al. | 424/401 |
| 6,548,050 B1 | 4/2003 | Bara | 424/64 |
| 6,685,952 B1 | 2/2004 | Ma et al. | 424/401 |
| 6,696,049 B2 | 2/2004 | Vatter et al. | |
| 6,699,488 B2 * | 3/2004 | Deckner et al. | 424/401 |
| 6,747,115 B2 | 6/2004 | Sakuta | 528/31 |
| 6,793,929 B2 | 9/2004 | Bleckmann et al. | 424/401 |
| 7,166,276 B2 * | 1/2007 | Stephens et al. | 424/63 |
| 7,175,835 B1 * | 2/2007 | Simoulidis et al. | 424/59 |
| 7,416,735 B2 * | 8/2008 | El-Nokaly et al. | 424/400 |
| 7,807,188 B2 * | 10/2010 | Hoath et al. | 424/401 |
| 2002/0028184 A1 | 3/2002 | Sunkel et al. | 424/59 |
| 2002/0106385 A1 | 8/2002 | Vatter et al. | 424/401 |
| 2002/0142018 A1 * | 10/2002 | Scholz et al. | 424/401 |
| 2003/0170193 A1 | 9/2003 | Pate et al. | 424/70.12 |
| 2003/0211061 A1 | 11/2003 | Deckner et al. | 424/70.1 |
| 2003/0211069 A1 | 11/2003 | Deckner et al. | 424/70.16 |
| 2003/0228339 A1 * | 12/2003 | El-Nokaly et al. | 424/401 |
| 2004/0146472 A1 | 7/2004 | Nakanishi | 424/70.12 |
| 2004/0228821 A1 | 11/2004 | Sunkel et al. | 424/70.12 |
| 2004/0235693 A1 | 11/2004 | Wei et al. | 510/130 |
| 2005/0008600 A1 | 1/2005 | Nakanishi et al. | |
| 2005/0089486 A1 | 4/2005 | Spindler et al. | 424/59 |
| 2005/0118218 A1 | 6/2005 | Cassin | 424/401 |
| 2005/0163812 A1 * | 7/2005 | Hoath et al. | 424/400 |
| 2006/0013790 A1 | 1/2006 | Shimizu | 424/70.12 |
| 2006/0057927 A1 | 3/2006 | Kang et al. | 445/46 |
| 2006/0078524 A1 | 4/2006 | Midha et al. | 424/70.12 |
| 2006/0078527 A1 | 4/2006 | Midha et al. | 424/70.27 |
| 2006/0079422 A1 | 4/2006 | Midha et al. | 510/130 |
| 2006/0100004 A1 | 5/2006 | Kim et al. | 455/575.3 |
| 2006/0111490 A1 | 5/2006 | Fonolla Moreno | 524/211 |
| 2006/0120979 A1 | 6/2006 | Rubin | 424/62 |
| 2006/0127344 A1 | 6/2006 | Zofchak et al. | 424/70.31 |
| 2007/0009463 A1 | 1/2007 | Niebauer et al. | 424/70.7 |
| 2007/0020217 A1 | 1/2007 | Themens | 424/70.12 |
| 2007/0173599 A1 | 7/2007 | Liu et al. | |
| 2008/0299058 A1 | 12/2008 | Saito et al. | |
| 2008/0299156 A1 | 12/2008 | Fares et al. | 424/401 |
| 2008/0311058 A1 | 12/2008 | Lou et al. | |
| 2009/0155321 A1 | 6/2009 | Harichian et al. | 424/401 |
| 2009/0226498 A1 | 9/2009 | Flugge-Berendes et al. | 424/411 |
| 2009/0247445 A1 * | 10/2009 | Lou et al. | 510/159 |

FOREIGN PATENT DOCUMENTS

| | | |
|---|---|---|
| DE | 100 49 041 | 4/2002 |
| EP | 0 009404 | 4/1980 |
| EP | 0 160 430 | 11/1985 |
| EP | 0 818 190 | 1/1998 |
| EP | 1 741 422 | 1/2007 |
| GB | 1 465 528 | 2/1974 |
| GB | 1 465 529 | 2/1974 |
| GB | 1 465 530 | 2/1974 |

(Continued)

OTHER PUBLICATIONS

Shin-Etsu, Silicone for Personal Care, 2002.* Shin-Etsu, Silicone products for Personal Care, 2005.*
Co-pending application for: Lou et al.; Case No. J9051(C); U.S. Appl. No. 11/820,382, filed Jun. 18, 2007, entitled Stable High Internal Phase Emulsions and Compositions Comprising the Same.
Co-pending application for: Lou et al.; Case No. J9075(C); U.S. Appl. No. 12/060,437, filed Apr. 1, 2008, entitled In-Shower and Bath Compositions.
International Search Report and Written Opinion on Application No. PCT/EP2010/052710 dated Jul. 27, 2010.
Co-pending application for: Applicant: Lou et al.; U.S. Appl. No. 12/784,046, filed May 21, 2010, entitled Topical Composition Comprising a Chaotrope.

(Continued)

*Primary Examiner* — Mark Eashoo
*Assistant Examiner* — M. Reza Asdjodi
(74) *Attorney, Agent, or Firm* — Edward A. Squillante, Jr.

(57) ABSTRACT

A method and composition for evenly applying water soluble actives is described. The method includes applying a composition with a HIPE to skin and generating a film having a hydrophilic surface so that composition and active can be evenly applied.

12 Claims, No Drawings

FOREIGN PATENT DOCUMENTS

| | | |
|---|---|---|
| GB | 2 139 919 | 11/1984 |
| GB | 2 181 737 | 4/1987 |
| JP | 57-091733 | 6/1982 |
| JP | 11-158032 | 6/1999 |
| JP | 2005-314327 | 11/2005 |
| WO | 96/21721 | 7/1996 |
| WO | 97/33560 | 9/1997 |
| WO | 01/00141 | 1/2001 |
| WO | 01/89464 | 11/2001 |
| WO | 03/022235 | 3/2003 |
| WO | 03/075879 | 9/2003 |
| WO | 2008/155228 | 12/2008 |
| WO | 2009/121787 A1 | 10/2009 |
| WO | 2010/009989 | 1/2010 |
| WO | 2010/045163 A2 | 4/2010 |

OTHER PUBLICATIONS

Co-pending application for: Applicant: Lou et al.; U.S. Appl. No. 12/814,855, filed Jun. 14, 2010, entitled High Humectant High Internal Phase Emulsion.

Co-pending Application: Applicant: Lou et al.,; U.S. Appl. No. 12/784,046, filed May 21, 2010.

Co-pending Application: Applicant: Lou et al.; U.S. Appl. No. 12/814,855, filed Jun. 14, 2010.

Co-pending Application: Applicant: Lou et al.; U.S. Appl. No. 11/820,382, filed Jun. 18, 2007.

Co-pending Application: Applicant: Lou et al.; U.S. Appl. No. 12/060,437, filed Apr. 1, 2008.

Co-pending Application: Applicant: Camali; U.S. Appl. No. 12/627,566, filed Nov. 30, 2009.

Co-pending Application: Applicant: Lou et al., U.S. Appl. No. 12/855,348, filed Aug. 12, 2010.

Co-pending Application: Applicant: Camali et al., U.S. Appl. No. 12/909,874, filed Oct 22, 2010.

*Shin-etsu Silicones for Personal Care*. Shin-Etsu Product Brochure, Emulsifiers Series; pp. 1-5.

Abstract of DE 100 49 041—published Apr. 11, 2002.

Abstract of JP 57-091733—published Jun. 8, 1982.

Abstract of WO 03/022235—published Mar. 20, 2003.

\* cited by examiner

METHOD AND COMPOSITION FOR EVENLY APPLYING WATER SOLUBLE ACTIVES

FIELD OF THE INVENTION

The present invention is directed to a method and composition for evenly applying water soluble actives. More particularly, the invention is directed to a method whereby an end use composition comprising a high internal phase emulsion (HIPE) with a water soluble active is applied to dry skin so that such active may be evenly distributed. The end use composition used in the method of this invention has a contact angle against water which is greater than about 90° before application and less than about 70° immediately after application with shear.

BACKGROUND OF THE INVENTION

Skin conditioning methods that provide, for example, moisturizing, lightening or sunless tanning benefits are known. Typically, such conditioning compositions are in the form of lotions meant to be applied to the skin subsequent to bathing and throughout the day, if necessary.

Many consumers find it desirable to deliver skin benefits via methods that rely on the application of topical compositions after showering. Unfortunately, however, such methods comprise actives that often are not uniformly distributed after application, thus leaving uneven and/or blotchy results after topically applying compositions to skin. Consumers try to prevent such uneven results by over applying composition, resulting in waste of composition in an attempt to achieve desired benefits. Moreover, many consumers are unsatisfied with the topical compositions they use since the same often yield ineffective results; leave a wet-feeling sensation after use or both. This can be true when conventional compositions are over applied to dry skin.

It is of increasing interest to develop a method and composition suitable to deliver a water soluble active, especially on dry skin, whereby the method and composition are effective for evenly distributing active and do not result in skin having a wet-feeling sensation. This invention, therefore, is directed to a method whereby topical composition comprising a HIPE and a water soluble active is applied to dry skin, resulting in water-soluble active that is evenly distributed. The topical composition employed in the method of this invention has a contact angle against water which is greater than about 90° before application and less than about 70° immediately after application with shear.

Additional Information

Efforts have been disclosed for making insoluble skin conditioning compositions. In U.S. Pat. No. 6,699,488, rinseable compositions with high internal phase emulsions are described.

Other efforts have been disclosed for making skin care compositions. In U.S. Pat. No. 6,696,049, cosmetic compositions with emulsifying cross-linked siloxane elastomer are described.

Still other efforts have been disclosed for making skin care compositions. In U.S. Pat. No. 5,908,707, cleaning articles having a high internal phase inverse emulsion are described.

Even other efforts have been disclosed for making skin care compositions. In U.S. Pat. No. 5,833,973, skin treatment compositions with a cross-linked non-emulsifying siloxane elastomer are described.

None of the additional information above describes a method whereby water soluble active is evenly applied to dry skin in the absence of generating a wet-feeling sensation.

SUMMARY OF THE INVENTION

In a first aspect, the present invention is directed to a method for evenly applying a water soluble active, the method comprising the steps of:
(a) applying to dry skin a topical composition comprising a water-in-oil HIPE, the HIPE comprising:
  1) water;
  2) emulsifier;
  3) steric stabilizer;
  4) depletion stabilizer;
  5) oil;
  6) non-emulsifying elastomer; and
  7) water soluble active; and
(b) shearing the topical composition during application onto skin resulting in free water creating a hydrophilic surface on the topical composition applied while simultaneously maintaining water in the HIPE for the water soluble active wherein the topical composition, prior to applying, has a contact angle against water which is greater than about 90° and less than about 70° immediately after topically applying with shear.

In a second aspect, the present invention is directed to a hydrophobic composition comprising a water-in-oil HIPE, the composition suitable for topical application with shear to ensure even distribution of active in the absence of generating a wet-feeling sensation.

All other aspects of the present invention will readily become apparent upon considering the detailed description and examples which follow.

HIPE, as used herein, means a high internal phase, water-in-oil emulsion where the emulsion is hydrophobic and at least about 73% by weight water when deplete of active. Topical composition, as used herein, means a hydrophobic end use composition comprising the HIPE with an active (or skin benefit agent) in the water phase of the HIPE, whereby the same is externally hydrophobic and is suitable for use on humans to result in a skin benefit like, for example, sunless tanning. Such a composition is meant to include product that may be applied, and preferably, is applied to skin which is dry. The HIPE used in the method of this invention (when comprising active) preferably makes up at least about 70% by weight of the total weight of the topical composition. It is, however, within the scope of the invention for the HIPE to make up to 100% of the cosmetically acceptable carrier used in the topical composition. Free water to create a hydrophilic surface means typically from about 20 to about 90%, and preferably, from about 35 to about 80% of the water, (based on total amount of water), in the topical composition exits to the surface to create a hydrophilic surface.

Skin, as used herein, is meant to include skin on the face, neck, chest, back, arms, hands, legs, buttocks and scalp (including hair). Steric stabilizer, as used herein, means an ingredient like a polymer (including elastomer) that prevents coalescence of water thereby stabilizing the HIPE. Active and skin benefit agent are meant to mean the same, and thus, may be used interchangeably, where the same include an ingredient that improves a skin characteristic, including a sunless tanning agent like dihydroxyacetone. Depletion stabilizer is meant to mean an agent that stabilizes the topical composition by surrounding water droplets. Non-emulsifying elastomer is defined to mean a siloxane from which polyoxyalkylene units are absent. Contact angle, as used herein, means the angle a water droplet makes on the surface of the topical composition taken before and immediately after shearing as determined with a Kruss OCA-20 Ganiometer.

Unless explicitly stated otherwise, all ranges described herein are meant to include all ranges subsumed therein. The term comprises is meant to encompass the terms consisting essentially of and consisting of: Furthermore, unless defined otherwise, the amount of polymer or elastomer used means the amount of cross-linked polymer and carrier oil added as a mixture whereby the cross-linked polymer typically makes up from about 10 to about 35% by weight of the mixture, including all ranges subsumed therein. Viscosity, as used herein, means a fluid's internal resistance to flow taken, unless stated otherwise, at a shear rate of 1 $S^{-1}$ at ambient temperature with a strain controlled parallel plate rheometer (like those sold by T.A. Instruments under the Ares name). Results described herein are based on applying topical composition, with shear, to create a film of composition that is from about 20 to about 45 microns thick. Applying with shear (i.e., shearing) means rubbing on an identified area of skin at a rate from about 100 to about 10,000 1/second, and preferably, from about 300 to about 8,000 1/second. Wet-feeling sensation means feeling as if towel drying is necessary at a point after application is complete.

DETAILED DESCRIPTION OF THE PREFERRED EMBODIMENT

There is no limitation with respect to the type of emulsifier that may be used in this invention other than that the emulsifier is suitable for use in a HIPE which may be used in an end use composition suitable for topical application. Such emulsifier often has an HLB of less than about 9, preferably less than about 7, and most preferably, less than about 5. Illustrative examples of the type of emulsifier that may be used in this invention include those generally classified as polyether modified silicone surfactants like PEG/PPG-20/22 butyl ether dimethicone, PEG-3 dimethicone, PEG-9 methyl ether dimethicone, PEG-10 dimethicone, mixtures thereof or the like. The emulsifiers are made available from suppliers like Shin-Etsu and sold under the names KF-6012, KF-6015, KF-6016, and KF-6017, respectively. Another emulsifier suitable for use is DC5225C made commercially available by Dow Corning. In an often preferred embodiment, the emulsifier used in this invention is PEG-10 dimethicone, KF-6017, DC5225C or a mixture thereof.

Typically, the emulsifier makes up from about 0.5 to about 12%, and preferably, from about 0.8 to about 10%, and most preferably, from about 1 to about 5% by weight of the HIPE, based on total weight of HIPE and including all ranges subsumed therein.

The steric stabilizer that may be used in this invention to prevent coalescence of water and to stabilize the HIPE used in the composition and method of this invention is preferably an elastomer. Such a steric stabilizer is one which preferably has a refractive index of greater than about 1.4 at 25° C. Moreover, the steric stabilizer is often a cross-linked elastomer (such as a polyether and/or polyglycerine cross-linked silicone elastomer) where the cross-linking group preferably has a chain length from about 8 to about 26 carbon atoms.

Often preferred steric stabilizers suitable for use in this invention are cross-linked dimethicone elastomers like Dimethicone/PEG-10/15 Crosspolymer in Dimethicone (KSG-210 or KSG-240), Dimethicone Polyglycerin-3 Crosspolymer in Dimethicone (KSG-710), mixtures thereof or the like.

Such steric stabilizers are made commercially available, and especially, from suppliers like Shin-Etsu.

Typically, the amount of steric stabilizer (i.e., including carrier) employed is from about 0.1 to about 25%, and preferably, from about 0.5 to about 15%, and most preferably, from about 2.5 to 6%, based on total weight of the HIPE and including all ranges subsumed therein. In a preferred embodiment, the steric stabilizer used in this invention is KSG-210 or a derivative or mimic thereof.

The HIPE used in the method and composition of the present invention further comprises a depletion stabilizer which often is an alkyl modified cross-linked silicone elastomer (such as a polyether and/or polyglycerine cross-linked silicone elastomer) where the cross-linking group preferably has a chain length from about 8 to about 26 carbon atoms.

Illustrative examples of the types of depletion stabilizer suitable for use in this invention include PEG-15/Lauryl Dimethicone Crosspolymer in Mineral Oil (KSG-310), PEG-15/Lauryl Dimethicone Crosspolymer and Isododecane (KSG-320), PEG-15/Lauryl Dimethicone Crosspolymer in Triethylhexanoin (KSG-330), PEG-10/Lauryl Dimethicone Crosspolymer and PEG 15/Lauryl Dimethicone Crosspolymer in Squalane (KSG-340), Lauryl/Dimethicone/Polyglycerine-3 Crosspolymer in Triethylhexanoin (KSG-830), Lauryl Dimethicone/Polyglycerine-3 Crosspolymer in Squalene (KSG-840), mixtures thereof or the like.

When used, the amount of depletion stabilizer (including carrier) employed is typically from about 0.25 to about 20%, and preferably, from about 0.5 to about 15%, and most preferably, from about 2 to about 5% by weight, based on total weight of HIPE and including all ranges subsumed therein.

In a preferred embodiment, the weight ratio of depletion stabilizer to stearic stabilizer in the HIPE used in the method of this invention is from about 1:3 to about 3:1, and most preferably, from about 1:2 to about 2:1. In a most especially preferred embodiment, the amount of steric stabilizer used is equal to from about 1.1 to about 1.7, and preferably, from about 1.2 to about 1.5 times the amount by weight of depletion stabilizer used in the HIPE, including all ranges subsumed therein.

Oil suitable for use in the HIPE used in this invention is limited only to the extent that the same can be used in a composition that may be topically applied. The oil used in the HIPE is preferably silicon-based, and particularly, one classified as dimethicone (DMF-A6cs), a cyclodimethicone such as a D4, D5, or D6 or a mixture thereof whereby such oils are commercially available from suppliers like Shin-etsu. Other preferred oils suitable for use include dimethicone-based oils having a viscosity from about 3 cps to about 100 cps at ambient temperature and as determined on a Ubbelohde Viscometer. Such oils may be used alone or in combination with other oils suitable for use in topical compositions, like mineral oil and/or paraffin oil.

The oil within the HIPE used in the method and composition of this invention typically makes up from about 0.5 to about 23%, and preferably, from about 5 to about 18%, and most preferably, from about 10 to about 15% by weight of the HIPE, based on total weight of the HIPE and including all ranges subsumed therein.

In an especially preferred embodiment, less than about 60%, and preferably, less than about 50%, and most preferably, from about 2 to about 35% by weight of the total oil in the HIPE used in this invention is provided as carrier with elastomer.

The non-emulsifying elastomer that may be used in this invention is one which is suitable for use in a composition that may be applied topically. Illustrative non-limiting examples of the types of non-emulsifying elastomers that may be used in this invention include those that have an average number (Mn) molecular weight in excess of 2,000, preferably, in excess of 5,000, and most preferably, in the range from about 10,000 to about 20 million, including all ranges subsumed therein. The term "non-emulsifying" defines a siloxane from which polyoxyalkylene units are absent. Often, the elastomers are formed from a divinyl compound which has at least two free vinyl groups, reacting with Si—H linkages of a polysiloxane backbone. Such elastomer compositions are commercially available under the proposed CTFA name of Cyclomethicone and Vinyl Dimethicone Methicone Cross Polymer, delivered as 20-35% elastomer in a cyclomethicone carrier. A related elastomer composition under the CTFA name of Crosslinked Stearyl Methyl Dimethyl Siloxane Copolymer is available as Gransil SR-CYC (25-35% elastomer in a cyclomethicone carrier) from Grant Industries, Inc., Elmwood Park, N.J. The commercial products are typically further processed by subjecting them to a high pressure (approximately 5,000 psi) treatment in a Sonolator with recycling in 10 to 60 passes. Sonolation achieves a resultant fluid with elastomer average particle size ranging from 0.2 to 10 micron, preferably 0.5 to 5 micron. Viscosity is preferred often when ranging between 300 and 20,000 cps at 25° C., as measured by a Brookfield LV Viscometer (size 4 bar, 60 rpm, 15 sec). In an especially preferred embodiment, a most desired non-emulsifying elastomer is a cyclomethicone/dimethicone cross-polymer made commercially available by suppliers like Dow Chemical under the name DC9045, and Shin-Etsu under the name KSG-15 elastomer (with about 5-12% by weight cross-linked polymer in a cyclomethicone carrier).

Typically, the amount of non-emulsifying elastomer (including carrier), used in the HIPE of this invention is from about 1.5 to about 18%, and preferably, from about 2 to about 10%, and most preferably, from about 3 to about 8% by weight, based on total weight of the HIPE and including all ranges subsumed therein.

The topical composition comprising the HIPE and used in the method of the present invention typically further comprises actives or skin benefit agents suitable for addition to the water phase of the HIPE (i.e., water soluble actives). Such actives include self-tanning compounds like dihydroxyacetone (DHA), vitamins (especially, niacinamide), vitamin C and its water soluble derivatives, ammonium salts such as those classified as hydroxypropyltri($C_1$-$C_3$ alkyl)ammonium salts, substituted ureas, water soluble resorcinols (including those esterified with, for example, ferulic acid, vanillic acid or the like), 12-hydroxystearic acid, moisturizers like sugar derivatives, natural extracts, mixtures thereof or the like.

Illustrative sugar derivatives that may be used include alkylated versions of glucose, sucrose, galactose, xylose, ribose, fructose or mannose, or the like or a mixture thereof. The often preferred sugar derivative is methylglucose. The natural extracts that may be used include, for example, extract of pea, kudzu, yarrow, cucumber, comfrey, chamomile, or a mixture thereof.

The ammonium salts which may be used can be obtained from a variety of synthetic procedures, most particularly by hydrolysis of chlorohydroxypropyl tri($C_1$-$C_3$ alkyl)ammonium salts. A most preferred species of ammonium salt is 1,2-dihydroxypropyltrimonium chloride, wherein the $C_1$-$C_3$ alkyl is a methyl group.

Ordinarily the $C_1$-$C_3$ alkyl constituent on the quaternized ammonium group used will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, tolyoyl sulfate, acetate, citrate, tartrate, lactate, gluconate, and benzenesulfonate.

Illustrative examples of the types of substituted ureas that may be used in this invention include hydroxymethyl urea, hydroxyethyl urea, hydroxypropyl urea; bis(hydroxymethyl)urea; bis(hydroxyethyl)urea; bis(hydroxypropyl)urea; N,N'-di-hydroxymethyl urea; N,N'-di-hydroxyethyl urea; N,N'-di-hydroxypropyl urea; N,N,N'-tri-hydroxyethyl urea; tetra (hydroxymethyl)urea; tetra(hydroxyethyl)urea; tetra (hydroxypropyl)urea; N-methyl-N'-hydroxyethyl urea; N-ethyl-N'-hydroxyethyl urea; N-hydroxypropyl-N'-hydroxyethyl urea and N,N'-dimethyl-N-hydroxyethyl urea. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Other actives suitable for use in the water phase of the HIPE used in the method of this invention include alpha- and/or beta-hydroxycarboxylic acids, as well as antioxidants. When hydroxycarboxylic acids are employed, they preferably include α-hydroxyethanoic acid, α-hydroxypropanoic acid, α-hydroxyhexanoic acid, α-hydroxyoctanoic acid, α-hydroxydecanoic acid, α-hydroxydodecanoic acid, α-hydroxytetradecanoic acid, α-hydroxyhexadecanoic acid, γ-hydroxyoctadecanoic acid, α-hydroxyeicosanoic acid, α-hydroxydocosanoic acid, α-hydroxyhexacosanoic acid, α-hydroxyoctacosanoic acid, salts thereof, mixtures thereof or the like.

Antioxidants suitable for use include diadzein, genistein, gallic acid, epicatechin, epigallacatechin, epicatechin-3-gallate, epigallocatechin-3-gallate, mixtures thereof or the like.

Even other actives may be combined in the topical compositions with the HIPE of the present invention (as actives or co-actives within the water phase and/or oil phase). For example, the topical compositions prepared with the HIPE used in the method of this invention may optionally contain a humectant. Suitable humectants are polyhydric alcohols intended for moisturizing, reducing scaling and stimulating removal of built-up scale from the skin. Typical polyhydric alcohols include polyalkylene glycols and more preferably glycerol (or glycerine), alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. Amounts of humectant may range (if used) anywhere from about 0.01 to 20%, preferably from about 0.01 to about 15%, optimally from about 0.75 to about 12% by weight of the end use composition. In yet another preferred embodiment, glycerin is used in the HIPE, either alone or in a mixture with DHA.

Still other illustrative additives suitable for use in the compositions used in the method of this invention include resorcinols, retinoids, including retinoic acid, retinal and retinyl esters as well as conjugated linoleic acid (CLA) and/or petroselinic acid, including derivatives thereof.

CLA isomers of the greatest interest in the present invention are cis 9, trans 11-linoleic acid and trans 10, cis 12-linoleic acid. Hereinafter the term "9,11-linoleic" or "10,12-linoleic" shall mean preferentially these two main isomers, but will include lesser amounts of the remaining isomers, particularly when obtained or derived from a natural source.

In accordance with the present invention, 9,11-linoleic acid and 10,12-linoleic acid may be formulated into the HIPE of this invention either as the free acid, as individual chemical derivatives, or as combinations of the free acid and derivative.

By "c9, t11, and 10, c12 isomer enriched CLA" is meant that at least 30% by weight of the total CLA (and/or CLA moieties) that may be present in the HIPE is in the form of the cis 9, trans 11 and trans 10, c is 12 isomers. Preferably, and when used, at least 40%, most preferably at least 50%, by weight of the total CLA and/or CLA moieties present in the HIPE, is in the form of the aforementioned isomers.

Commercially, CLA is available as Clarinol® A-80 and A-95 from Loders-Croklaan, Channahon, Ill. and Neobee® CLA 80 and 90 from Stepan, North Field, Ill.

Typically, the amount of active or skin benefit agent used in the water phase of the HIPE of this invention is, collectively, from about 0.5 to less than about 30%, and preferably, from about 1 to about 25%, and most preferably, from about 1.5 to about 7%, based on total weight of the HIPE and including all ranges subsumed therein. An often preferred active used in the method of this invention is DHA.

Water will typically make up the balance of the HIPE, and should make up at least about 73% (when no active is present) to typically no more than about 96% by weight of the HIPE, including all ranges subsumed therein.

Preservatives may also be incorporated into the topical compositions used in this invention to protect against the growth of potentially harmful microorganisms. While it is in the aqueous phase that microorganisms tend to grow, microorganisms can also reside in the oil phase. As such, preservatives which have solubility in both water and oil are preferably employed in the end use compositions described herein. Suitable traditional preservatives are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, imidazolidinyl urea, sodium dehydroxyacetate and benzyl alcohol. The preservatives should be selected having regard for the use of the HIPE and possible incompatibilities between the preservatives and other ingredients in the emulsion. Preservatives are preferably employed in amounts ranging from 0.01% to 2% by weight of the topical composition.

Conventional thickeners may optionally be used in the topical compositions used in the method of this invention. Illustrative examples include those commercially sold under the names Aristoflex® AVC (acryloyl dimethyltaurate/vinyl pyrrolidone copolymer), Sepigel®305 (polyacrylaamide/$C_{13-14}$ isoparrafin/laureth-7), Simulgel®EG (sodium acrylate/sodium acryloyidimethyl taurate copolymer/isohexadecane/polysorbate 80), Carbopol 934 (crosslinked polyacrylate), Stabylen®30 (acrylates/vinyl isodecanoate crosspolymer) mixtures thereof or the like. The preferred thickener is Aristoflex®AVC made commercially available by Clairiant Corporation. Typically, when employed, the thickener makes up from about 0.01 to about 5.0% by weight of the topical composition, including all ranges subsumed therein.

Sunscreens may be used (in any desirable combination) in the compositions used in the method of this invention and they include those materials commonly employed to block ultraviolet light. Illustrative compounds Avobenzene, available as Parsol 1789®, ethylhexyl-p-methoxycinnamate, available as Parsol MCX®, and benzophenone-3, also known as Oxybenzone. Inorganic sunscreen actives may be employed such as microfine titanium dioxides, polyethylene and various other polymers. The exact amount of sunscreen employed in the compositions can vary depending upon the degree of protection desired from the sun's UV radiation.

Even other optional actives may be used with the topical compositions used in this invention and they include physical scatterers (like $TiO_2$ and/or ZnO), chelators (like EDTA), microspheres (e.g., polyethylene based spheroids sold under the name CL-2080; ethylene and methacrylate based spheroids sold under the names SPCAT-12 and DSPCS-12, respectively, made available by Kobo Industries), anti-inflammatory agents (including the standard steroidal and non-steroidal types), and dispersants (e.g., PEG-100 stearate and/or NaCl).

When cosmetically acceptable carriers are desired in the topical compositions used in this invention (acting as co-carriers with the HIPE) such carriers may be selected from hydrocarbons, fatty acids, fatty alcohols and esters. Petrolatum is the most preferred hydrocarbon type of emollient conditioning agent. Other hydrocarbons that may be employed include mineral oil, polyolefins such as polydecene, and paraffins such as isohexadecane (e.g., Permethyl 99® and Permethyl 101®).

Fatty acids and alcohols suitable for use as carriers often have from 10 to 30 carbon atoms. Illustrative of this category are pelargonic, lauric, myristic, palmitic, steric, isosteric, hydroxysteric, oleic, linoleic, ricinoleic, arachidic, behenic and erucic acids and alcohols.

Oily ester emollients suitable for use as cosmetically acceptable carriers in topical compositions used in the method of this invention can be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil.
2. Acetoglyceride esters, such as acetylated monoglycerides.
3. Ethoxylated glycerides, such as ethoxylated glyceryl monostearate.
4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
5. Alkenyl esters of fatty acids having 10 to 20 carbon atoms. Examples thereof include oleyl myristate, oleyl stearate, and oleyl oleate.
6. Ether-esters such as fatty acid esters of ethoxylated fatty alcohols.
7. Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and difatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.

8. Wax esters such as beeswax, spermaceti, myristyl myristate, stearyl stearate.

In a preferred embodiment the HIPE of this invention makes up at least about 70% by weight of the topical composition used, and most preferably, at least about 85 to about 96% by weight of the topical composition, including all ranges subsumed therein.

Minor adjunct ingredients may also be included such as fragrances, antifoam agents, and colorants, each in their effective amounts to accomplish their respective functions. In a preferred embodiment, the topical compositions used in the present invention are substantially free (i.e., less than about 1.0% by weight) of non-emulsifying elastomer, and most preferably, free of non-emulsifying elastomer.

When making the topical compositions used in the method of the present invention, the desired ingredients can be mixed in no particular order and usually at temperatures from about ambient to about 65° C. and under atmospheric pressure. In a preferred embodiment, however, water with water soluble active dissolved therein is added to oil, and the HIPE is made prior to adding cosmetically acceptable carriers (i.e., co-carriers). Typically mixing occurs at about moderate shear.

The topical compositions prepared with the HIPE and used in the method of this invention preferably have an initial viscosity of less than about 6000 cps, and most preferably, from about 10 to about 4000 cps, including all ranges subsumed therein.

The compositions used in the present invention typically have an initial (i.e., before application) water droplet diameter size from about 10 to about 100 microns (preferably from about 15 to about 65 microns) whereby after application to dry skin the same will unexpectedly have a water droplet diameter size reduction such that the final water droplet diameter size (i.e., the diameter of water droplets in the HIPE forming a portion of the topical compositions and during application) is unexpectedly from about 5 to about 20, and preferably, from about 8 to about 15 times smaller than the initial water droplet diameter size. Water droplet size may be measured, for example, by using confocal microscopy.

In a most especially preferred embodiment, the topical compositions used in the method of the present invention have a Capillary Number greater than 1 and less than about 1.6. Such compositions have a contact angle of greater than about 90° before application. Immediately after application with shear and according to the method of this invention, the topical compositions employed will comprise a contact angle of less than about 70°, and preferably, between about 55 to about 70° as determined using a Kruss OCA-20 Ganiometer.

The method of this invention unexpectedly results in compositions with a hydrophobic exterior having a hydrophilic surface during application to dry skin. The same is surprisingly achieved as water exits the HIPE of the topical composition during application and rests or congregates on the surface of the composition applied to skin. Surprisingly, therefore, the subsequent addition of composition to dry skin having topical composition applied thereon causes new composition with a hydrophic exterior to slide or slip over composition already having been applied and with a hydrophilic surface. Such an unexpected result allows for even application of water soluble actives as well as homogeneous results on skin and less topical composition being used since over application is prevented. Moreover, the compositions of the present invention lose (e.g., via evaporation/drying) from about 45 to about 75% by weight of their total water within about 200 seconds from application yet retain from about 15 to about 50% by weight of their total water after about 600 seconds from application. Such a result (i.e., rapid drying with water retention) allows for excellent distribution of active in the absence of a wet-feeling sensation.

The packaging for the compositions used in the method of this invention is not limited and often is a bottle, tube, roll-ball applicator, squeeze container or lidded jar.

The following examples are provided to facilitate an understanding of the present invention. The examples are not intended to limit the scope of the claims.

EXAMPLE 1

Topical compositions comprising HIPE and suitable for sunless tanning were prepared by combining the following ingredients under moderate shear.

| Ingredient | Percent by Weight |
| --- | --- |
| Glycerin | 4-12 |
| Dihydroxyacetone | 2.5 |
| Thickener (Aristoflex AVC) | 0-3 |
| Dimethicone (Cyclic D5) | 3-10 |
| Silicone oil (DMF A-6cs) | 1-4 |
| Emulsifier (DC5225C) | 1-3 |
| Steric stabilizer (KSG 210) | 1-3 |
| Depletion stabilizer (KSG 340) | 1-2 |
| Non-emulsifying elastomer (KSG 15) | 2-6 |
| Microspheres (CL 2080) | 2-5 |
| Water | Balance |

EXAMPLE 2

The compositions prepared in Example 1 were topically applied to forearms of panelists. Commercially available sunless tanning products (controls comprising oil-in-water emulsion) were also applied for bilateral comparisons. All panelists concluded that the topical composition applied and made according to this invention perceptually dried faster and overall resulted in a better skin feel when compared to the controls.

EXAMPLE 3

The compositions prepared in Example 1 were topically applied to the forearms of panelists as were commercially available sunless tanning products similar to those described in Example 2. Assessment of usage revealed that about 10 to about 20% less product made according to this invention was needed to adequately cover skin, a result of the hydrophilic surface created during application of the product of this invention and the slip affect created by applying additional composition having an oil-based (i.e., hydrophobic) exterior.

EXAMPLE 4

The drying profile of the topical compositions made in Example 1 (applied according to this invention) were compared to commercially available sunless tanning products as described in Example 1. The profile was determined by spreading and shearing, with a doctor blade, composition on a slide (about 25 microns thick) and weighing the slide over time. The results in the table demonstrate that the topical compositions comprising HIPE and applied according to this invention dried faster yet retained more water than commercially available sunless tanning products. The data shows that water remains in the composition of this invention for effective active functioning notwithstanding the fact that the composition dries faster to prevent a consumer perceived wet-feeling sensation.

TABLE

| Composition | Percent reduction in composition weight over time (seconds) | | | | |
|---|---|---|---|---|---|
| | 0 | 100 sec | 200 sec | 400 sec | 600 sec |
| 1* | — | 51% | 65% | 68% | 71% |
| 2* | — | 37% | 54% | 59% | 61% |
| 3* | — | 31% | 46% | 53% | 55% |
| Control** | — | 13% | 24% | 40% | 51% |
| Control*** | — | 16% | 29% | 48% | 71% |

*Compositions made consistent with this invention.
**Olay ® water-in-oil sunless tanning product with DHA.
***Olay ® oil-in-water sunless tanning product with DHA.

What is claimed is:

1. A method for evenly applying a water soluble active, the method comprising the steps of:
   (a) applying to dry skin a topical composition comprising a water-in-oil HIPE, the HIPE comprising:
      1) water;
      2) emulsifier from about 0.5 to 12% by weight;
      3) steric stabilizer comprising a polyether or polyglycerine cross-linked silicone elastomer or both;
      4) depletion stabilizer comprising an alkyl modified cross-linked silicone elastomer where the cross-linking group has a chain length from about 8 to about 26 carbon atoms;
      5) oil;
      6) non-emulsifying elastomer, and
      7) water soluble active; and
   (b) shearing the topical composition during application onto the skin resulting in free water creating a hydrophilic surface on the topical composition applied while simultaneously maintaining water in the HIPE for the water soluble active
   wherein the topical composition, prior to applying, has a contact angle against water which is greater than about 90° and less than about 70° immediately after topically applying with shear and further wherein the weight ratio of depletion stabilizer to steric stabilizer in the HIPE is from about 1:3 to about 3:1.

2. The method according to claim 1 wherein the contact angle of the composition is from about 55 to about 70° immediately after topically applying the composition with shear.

3. The method according to claim 1 wherein the emulsifier has an HLB of less than about 9.

4. The method according to claim 1 wherein water exits the HIPE of the composition to create a hydrophilic surface on the composition during application.

5. The method according to claim 1 wherein additional composition having a hydrophobic exterior is applied and slips over hydrophilic surface of previously applied composition.

6. The method according to claim 1 wherein from about 45 to about 75% by weight water in the topical composition is lost after about 200 seconds from application.

7. The method according to claim 1 wherein water soluble active is evenly distributed in the absence of generating a wet-feeling sensation.

8. The method according to claim 1 wherein the water soluble active is DHA.

9. A topical composition comprising a HIPE as used in the method of claim 1.

10. The topical composition comprising according to claim 9 wherein the topical composition is externally hydrophobic before application and externally hydrophilic after application with shear.

11. The composition according to claim 9 wherein the composition has a contact angle against water of greater than about 90° before application and from about 55 to about 70° immediately after application with shear.

12. The method according to claim 1 wherein the HIPE consists essentially of ingredients 1 through 7.

\* \* \* \* \*

UNITED STATES PATENT AND TRADEMARK OFFICE
CERTIFICATE OF CORRECTION

| | | |
|---|---|---|
| PATENT NO. | : 8,299,127 B2 | Page 1 of 1 |
| APPLICATION NO. | : 12/402238 | |
| DATED | : October 30, 2012 | |
| INVENTOR(S) | : Anjing Lou and Qiang Qui | |

It is certified that error appears in the above-identified patent and that said Letters Patent is hereby corrected as shown below:

On the Title page item (75), the inventors' names were inverted. "Lou Anjing" and "Qiu Qiang" should have read as follows; please correct as follows:
-- Anjing Lou
   Qiang Qiu --

Signed and Sealed this
Thirtieth Day of April, 2013

Teresa Stanek Rea
*Acting Director of the United States Patent and Trademark Office*